United States Patent [19]
Pagan

[11] Patent Number: 6,024,730
[45] Date of Patent: Feb. 15, 2000

[54] CATHETER ASSEMBLIES AND INNER CANNULAE

[75] Inventor: Eric Pagan, Kent, United Kingdom

[73] Assignee: Smiths Industries plc, London, United Kingdom

[21] Appl. No.: 08/962,734

[22] Filed: Nov. 3, 1997

[30] Foreign Application Priority Data

Nov. 8, 1996 [GB] United Kingdom .................. 9623402

[51] Int. Cl.⁷ .................................................. A61M 5/00
[52] U.S. Cl. ........................... 604/264; 130/110; 604/280
[58] Field of Search .................................. 604/264, 280; 138/118, 119, 120, 121

[56] References Cited

U.S. PATENT DOCUMENTS

| | | |
|---|---|---|
| 4,801,297 | 1/1989 | Mueller . |
| 4,852,565 | 8/1989 | Eisele ................................ 604/264 X |
| 5,507,751 | 4/1996 | Goode et al. ........................... 604/264 |

FOREIGN PATENT DOCUMENTS

| | | |
|---|---|---|
| 0215173A1 | 3/1987 | European Pat. Off. . |
| 0430542A2 | 6/1991 | European Pat. Off. . |
| 22308806 | 4/1989 | United Kingdom . |
| 2285583 | 7/1995 | United Kingdom . |
| WP96/06653 | 3/1996 | WIPO . |
| WP96/38193 | 12/1996 | WIPO . |

*Primary Examiner*—Wynn Wood Coggins
*Assistant Examiner*—N. Kent Gring
*Attorney, Agent, or Firm*—Pollock, Vande Sande & Amernick

[57] ABSTRACT

An inner cannula for a tracheostomy tube assembly is formed from a tubular member having two parallel rows of slots formed along its length and covered by a sheath of thin flexible material on the inside of the tubular member, so that the slots can freely open and close on flexing. The two rows of slots are separated from one another by two longitudinal regions uninterrupted by slots, which give the cannula axial rigidity.

17 Claims, 1 Drawing Sheet

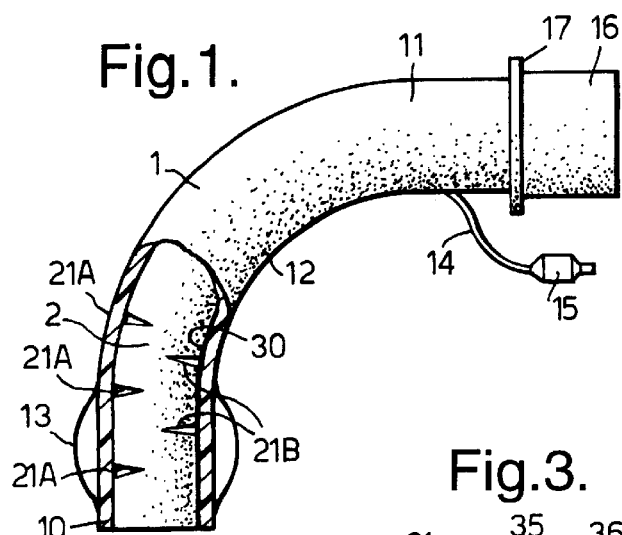
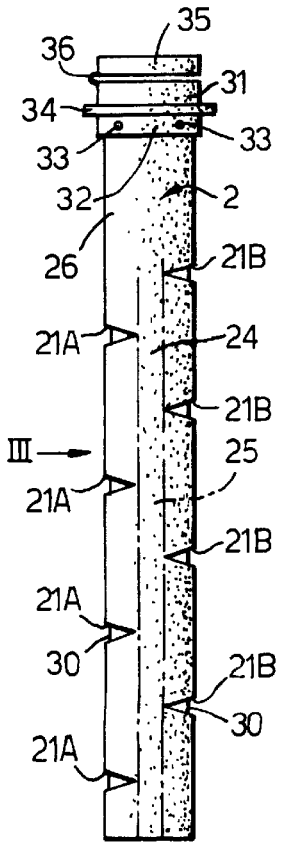
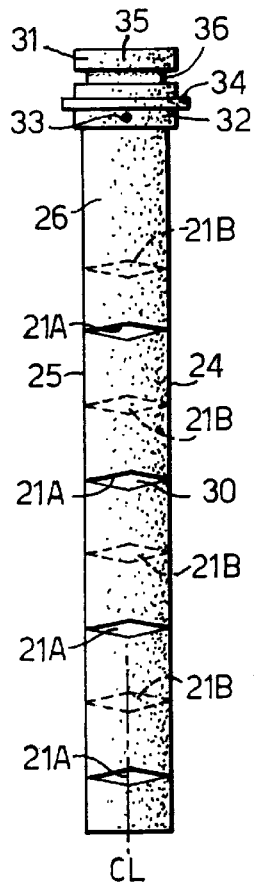
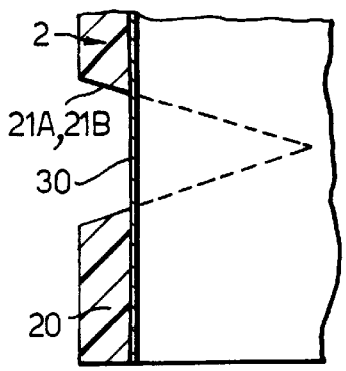
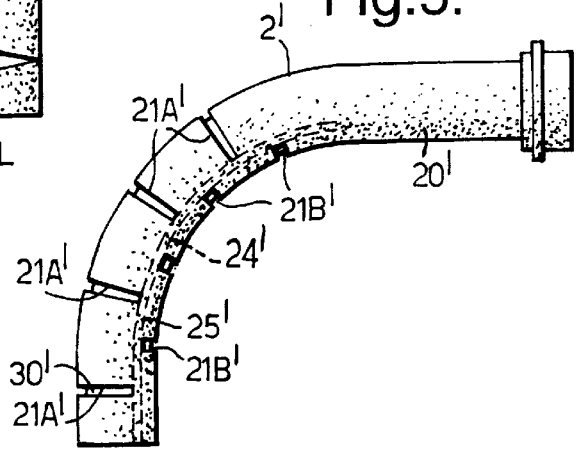

CATHETER ASSEMBLIES AND INNER CANNULAE

BACKGROUND OF THE INVENTION

This invention relates to catheter assemblies and inner cannulae for such assemblies.

The invention is more particularly concerned with catheter assemblies having a catheter and a removable inner cannula.

Some catheter assemblies, such as tracheostomy tubes, have an inner cannula, which is removable from the catheter. By removing and replacing the inner cannula, the secretions that build up within the catheter can be removed without the need to replace the catheter itself. This can reduce the risk of infection and, by avoiding the need to remove the catheter, it can reduce the discomfort, disturbance and trauma caused to the patient.

Although an inner cannula can have advantages, it can reduce the flow through the catheter because the fluid must flow through the inner cannula, which has a smaller internal diameter than that of the catheter itself. Thus, it is desirable that the wall of the inner cannula be as thin as possible and that it be a close fit within the catheter. Where the tracheostomy tube is of a radial shape, that is, it is curved along its entire length, the inner cannula can be similarly shaped so it does not need to bend during insertion, thereby enabling it to be relatively rigid. It is preferable, however, in some cases to use a tracheostomy tube with an anatomical design, in which opposite ends of the tube are relatively straight and linked by a curved section midway. With such a tube, the inner cannula must be able to flex as it is inserted and removed. In an attempt to make the inner cannula as thin as possible and to enable it to flex, the cannula may tend to buckle during insertion and may cause a restriction in flow. To prevent buckling, a circumferentially-corrugated cannula may be used but the corrugations of this can impede gas flow along the catheter appreciably as a result of the reduction in internal diameter and turbulence.

BRIEF SUMMARY OF THE INVENTION

It is an object of the present invention to provide an improved catheter assembly and inner cannula.

According to one aspect of the present invention there is provided a cannula comprising a tubular member having a plurality of slots spaced from one another along the member, each of the slots extending around a part of the circumference of the member so as to increase the flexibility of the member, and the cannula having means occluding the opening through the slots without substantially impeding the ability of the slots to open and close.

The slots are preferably located in two rows extending along opposite sides of the tubular member. The width of each slot preferably exceeds its height, the width of each slot extending around a part of the circumference. The cannula may have a longitudinal region extending along the length of the cannula that is uninterrupted by the slots so to maintain axial rigidity of the cannula. Preferably, the cannula has two of the longitudinal regions extending parallel to one another. The cannula may be formed to have a natural straight shape or a natural curved shape in which case the slots may be located in a first row extending along the outer curve of the cannula and in a second row extending along the inner curve of the cannula. The slots in the first row are preferably wider than the slots in the second row. The tubular member may be of a plastics material. The means occluding the opening through the slots may be a sheath of material thinner and more flexible than the material of the tubular member. The sheath is preferably of a resilient material and may be applied to the inner surface of the tubular member. Alternatively, the sheath may be shrunk onto the outside of the tubular member. In another example, the means occluding the opening through the slots may be provided by a material filling the slots, which may be injected to fill the slots after injecting material to form the tubular member. One end of the tubular member may have a region uninterrupted by the slots.

According to another aspect of the present invention there is provided a catheter assembly comprising an outer catheter and an inner cannula according to the above one aspect of the invention inserted within said outer catheter.

According to a further aspect of the present invention there is provided a tracheostomy assembly comprising an outer tracheostomy tube and an inner cannula according to the above one aspect of the invention inserted within the outer tube.

A catheter assembly according to the present invention, in the form of a tracheostomy tube assembly, will now be described, by way of example, with reference to the accompanying drawings.

BRIEF DESCRIPTION OF THE DRAWINGS

FIG. 1 is a partly cut-away side elevation view of the assembly;

FIG. 2 is a side elevation view of the inner cannula;

FIG. 3 is a side elevation view of the cannula along the arrow III of FIG. 2;

FIG. 4 is an enlarged cross-sectional side elevation view of a part of the cannula; and FIG. 5 is a side elevation view of an alternative inner cannula.

DETAILED DESCRIPTION OF THE PREFERRED EMBODIMENTS

With reference to FIG. 1, the catheter assembly comprises a tracheostomy tube or catheter 1 and an inner cannula 2 within the tracheostomy tube.

The tracheostomy tube 1 is of a conventional form, having a patient end 10, which, in use, is inserted within the trachea of a patient, and a machine end 11, which extends at right angles to the patient end 10. In use, the patient end 10 is located in the trachea and the machine end 11 projects from a surgically-made opening in the neck of the patient. The tube 1 has an internal diameter between 3–11 mm. The patient end 10 and machine end 11 are substantially straight and are interconnected by an intermediate, curved region 12 so that the tube substantially complies with the patient's anatomy. An inflatable cuff 13 encircles the tube 1 close to the patient end 10 and is inflatable via an inflation line 14 and connector 15. The inflatable cuff 13 is not essential since many tracheostomy tubes do not have such a cuff. At the machine end 11 of the tube 1, a connector 16 and a flange 17 enable the tube to be held in position on the patient's neck.

With reference now also to FIGS. 2 to 4, the inner cannula 2 has an outer tubular sleeve 20 of a bendable plastics material with a wall thickness of about 0.3 mm. The sleeve 20 is straight and has a circular section and an external diameter slightly less than the internal diameter of the catheter 1, so that it can be inserted and withdrawn readily. The wall of the sleeve 20 is formed with eight slots 21A and 21B spaced from one another along the cannula and extending around a part of the circumference of the sleeve so as to increase its flexibility. Different numbers of slots could be used. The slots may be cut from the cannula or moulded with it. Four of the slots 21A are located in a row on one side of the sleeve 20; the other four slots 21B are located in a row on the opposite side of the sleeve 20. The slots 21A are separated from the slots 21B by two parallel, longitudinal regions 24 and 25, about 3 mm wide, that are not interrupted by the slots. The width of the longitudinal regions 24 and 25 need not be 3 mm; for example, the width could be less than this, such as twice the wall thickness. The slots 21A and 21B are of lozenge shape tapering towards their ends so that their height is greatest midway across their width, that is, midway between the regions 24 and 25, the width of the slots exceeding their maximum height. Slots of other shapes could, alternatively, be used. The slots 21A on one side alternate with the slots 21B on the other side along the length of the cannula. A part 26 of the length of the sleeve 20, towards its rear or machine end, does not have any slots.

The cannula 2 also has an inner sheath 30 secured to the inside of the sleeve 20 such as to cover and occlude the slots 21A and 21B. In this respect, the sheath 30 may extend along the entire length of the sleeve 20 or along only that region including the slots. The sheath 30 is thinner than the sleeve, typically being about 0.1 mm thick, and is of a flexible, resilient plastics material such as PVC. There are various ways in which the inner sheath 30 can be formed and be attached to the inside of the outer sleeve. For example, the sheath 30 could be blow moulded or insert moulded within the sleeve 20. Alternatively, the sheath 30 could be applied to the outside of the sleeve, such as by heat shrinking a sheath about the sleeve, or by dip moulding, or by wrapping a sheet of material around the sleeve. Adhesives, solvents or heat could be used to attach the sheath 30 securely to the sleeve 20.

At its rear or machine end, the sleeve 20 has a coupling 31 of the same material as the rest of the sleeve and with a thicker wall than the tube, so that it is rigid. The forward end 32 of the coupling 31 is a clip fit within the tracheostomy tube connector 16 by virtue of three radially-projecting pips 33, which engage forwardly of an internal lip (not shown) within the tracheostomy tube connector. A thin flange 34 projects radially from the coupling 31 towards its machine end, so as to limit the extent of insertion of the inner cannula 2. The rear end of the coupling 31 takes the form of a ring 35 hinged by a flexible web 36 to the forward part of the coupling, providing a ring-pull feature enabling the ring to be folded down to facilitate withdrawal of the inner cannula 2 from the tracheostomy tube 1. This feature is described in more detail in GB2205504. The outside of the inner cannula 2 may be lubricated or coated with a lubricious coating to reduce insertion forces.

The cannula 2 is axially rigid, that is, it does not expand along its length when pulled or contract when pushed axially, because of the two regions 24 and 25. The slots 21A and 21B, however, considerably increase the flexibility of the cannula 2, the flexibility being greatest in a plane including the center lines CL of the two series of slots, that is, the line extending at right angles to the length of the slots, midway along their length. Bending the cannula 2 in this plane in one sense causes the slots on one side to open and the slots on the other side to close; bending the cannula in the opposite sense closes the slots on the one side and opens the slots on the other side. The sheath 30 stretches over the slots that open and is compressed over the slots that close so that it provides very little restriction to flexing of the cannula. Even though the natural shape of the cannula is straight, it has sufficient flexibility to enable its use in tracheostomy tubes with a variety of different curves.

The flexibility of the inner cannula 2 enables it to bend readily to comply with the shape of the catheter 1, when the plane of flexibility of the cannula is aligned with the plane of curvature of the catheter, even though the catheter has two straight regions separated by a curved region. The inner cannula can be relatively thin compared with a corrugated cannula, so that air flow along the assembly is not significantly affected. The rear region 26 of the cannula does not need to bend because it lies in the straight, machine end of the catheter, so there is no need for this part of the cannula to be provided with slots. The regions 24 and 25 give the cannula axial rigidity so that it can be inserted within the outer catheter without any danger of the cannula collapsing axially, like a concertina. The inner sheath 30 gives the inside of the cannula a relatively smooth surface, thereby reducing gas turbulence that might otherwise be caused by the slots, and enables a suction catheter or other device to be inserted without snagging on the slots. Where, however, the sheath is on the outside of the sleeve, this can have advantages because secretions deposited inside the inner cannula will be less easily dislodged, because they collect in the recesses provided by the slots.

Instead of forming the inner cannula with a natural straight shape, it may be formed curved, as shown with the cannula 2' in FIG. 5. The sleeve 20' could be injection moulded with the curved shape or extruded and then given the desired curve by heat treatment. Two series of slots 21A' and 21B' are provided in the cannula, one series 21A' extending along the outer curve of the cannula and the other series 21B' extending along the inner curve. The outer slots 21A' are longer than the inner slots 21B' such that the two regions 24' and 25' uninterrupted by slots, which provide the axial rigidity of the cannula, are spaced from one another by about 45°. With a cannula preformed to shape in this way, the slots 21A' and 21B' on the outer and inner curve of the cannula are the same width when the cannula is in its natural shape, following the curvature of the outer catheter. The slots will open or close as the cannula 2' is deformed from its natural shape, during insertion and withdrawal. This cannula 2' has the advantage that the lining sheath 30' is only deformed from its natural condition during insertion and withdrawal and not while the cannula is located in the outer catheter 1 during use, so it is less stressed and provides a smoother surface. The cannula also requires less force to insert and remove than a straight cannula.

The openings provided by the slots need not be occluded by a sheath, but could be occluded by some other means, such as, for example, by filling the slots with a material that is softer, more resilient and flexible than the remainder of the cannula, so that the slots can still open and close and passage of material through the slots is prevented. A cannula with slots filled in this way could be made by a two-stage injection moulding technique where the filling material has a lower melting temperature than the main part of the cannula and is injected into the openings through the slots after injecting material to form the main part of the cannula. This arrangement enables the surface of the cannula to be smooth on the inside and outside.

It will be appreciated that the slots could be of different shapes and sizes, that they could be spaced unevenly along the inner cannula to provide maximum flexibility in selected regions. The cannula could have different numbers of slots.

The inner cannula is not confined to tracheostomy tube assemblies but could be used in other assemblies having an outer catheter and an inner cannula.

What I claim is:

1. A catheter assembly comprising an outer catheter and an inner cannula located within said outer catheter, said inner cannula comprising: a tubular member; a plurality of slots formed in said tubular member and spaced from one another along said tubular member, each said slot extending around a part of a circumference of said tubular member so as to increase the flexibility of said tubular member; and a member occluding the opening through each said slot on an inner surface of said cannula without substantially impeding the ability of said slots to open and close.

2. A tracheostomy assembly comprising an outer tracheostomy tube and an inner cannula located within said tracheostomy tube, said inner cannula comprising: a tubular member; a plurality of slots formed in said tubular member and spaced from one another along said tubular member, each said slot extending around a part of a circumference of said tubular member so as to increase the flexibility of said tubular member; and a member occluding the opening through each said slot on an inner surface of said cannula without substantially impeding the ability of said slots to open and close.

3. An assembly according to claim 1 or 2, wherein said slots are located in two rows extending along opposite sides of said tubular member.

4. An assembly according to claim 1 or 2, wherein said slots each have a width extending around the circumference of the cannula and a height extending longitudinally of the cannula, and wherein the width of each slot exceeds its height.

5. An assembly according to claim 1 or 2, wherein a longitudinal region extends along the length of said cannula and is uninterrupted by said slots so as to maintain axial rigidity of said cannula.

6. An assembly according to claim 4, wherein said cannula has two of said longitudinal regions extending parallel to one another.

7. An assembly according to claim 1 or 2, wherein said cannula is formed to have a natural straight shape.

8. An assembly according to claim 1 or 2, wherein said cannula is formed to have a natural curved shape.

9. An assembly according to claim 7, wherein said slots are located in a first row extending along an outer curve of the cannula and in a second row extending along an inner curve of said cannula.

10. An assembly according to claim 8, wherein said slots in said first row are wider than said slots in said second row.

11. An assembly according to claim 1 or 2, wherein said tubular member is of a plastics material.

12. An assembly according to claim 1 or 2, wherein said member occluding the opening through each said slot is a sheath of material thinner and more flexible than the material of said tubular member.

13. A cannula according to claim 11, wherein said sheath is of a resilient material.

14. An assembly according to claim 11, wherein said sheath is applied to an inner surface of said tubular member.

15. An assembly according to claim 1 or 2, wherein said member occluding the opening through each said slot is provided by a material filling each said slot.

16. An assembly according to claim 14, wherein said material is injected to fill said slots after injecting material to form said tubular member.

17. An assembly according to claim 1 or 2, wherein one end of said tubular member has a region uninterrupted by said slots.

* * * * *